US007585892B2

(12) United States Patent
Huang et al.

(10) Patent No.: US 7,585,892 B2
(45) Date of Patent: Sep. 8, 2009

(54) COMPOUND FOR PROMOTING THE GROWTH OF NEURAL CELLS

(75) Inventors: Chung-Yang Huang, Taipei (TW); Chia-Nan Chen, Taipei (TW); Wan-Zo Ho, Taipei (TW)

(73) Assignee: Naturewise Biotech & Medicals Corporation, Taipei (TW)

( * ) Notice: Subject to any disclaimer, the term of this patent is extended or adjusted under 35 U.S.C. 154(b) by 665 days.

(21) Appl. No.: 11/393,619

(22) Filed: Mar. 30, 2006

(65) Prior Publication Data

US 2007/0232534 A1    Oct. 4, 2007

(51) Int. Cl.
    *A61K 31/353*    (2006.01)
(52) U.S. Cl. ...................................... 514/456
(58) Field of Classification Search ............... 514/456
    See application file for complete search history.

(56) References Cited

FOREIGN PATENT DOCUMENTS

| JP | 2005-272374 A | 10/2005 |
| TW | 2005100975229 | 10/2008 |
| WO | WO2004/113318 A1 | 12/2004 |

OTHER PUBLICATIONS

Brian T. Murphy et al., Cytotoxic Flavanones of Schizolaena hystrix from the Madagascar Rainforest, 2005, pp. 417-419, Journal, J. Nat. Prod., American Chemical Society and American Society of Pharmacognosy.
J.D. Hare, Geographic and genetic variation in the leaf surface resin components of Mimulus aurantiacus from southern California, 2002, Journal, Biochemical Systematics and Ecology, vol. 30, pp. 281-296, Elsevier Science Ltd.
Mei-Huims Tseng et al., Allelopathic Potential of Macaranga tanarius (L.) Muell.-Arg, Journal, Journal of Chemical Ecology, vol. 29, No. 5, May 2003, Plenum Publishing Corporation.
Shigenori Kumazawa et al., A New Prenylated Flavonoid from Propolis Collected in Okinawa, Japan, Journal, Biosci. Biotechnol. Biochem., 68, pp. 260-262, 2004, JSBA.
Chia-Nan Chen et al., Propolin C from propolis induces apoptosis through activating caspases, Bid and cytochrome c release in human melanoma cells, Journal, Biochemical Pharmacology 67, 2004, pp. 53-66, Elsevier.
English Abstract of Chinese Office Action dated Oct. 10, 2008.
European Search Report, Jul. 21, 2006, EP06251426, Munich.

Chia-Nan Chen et al., Cytotoxic Prenylfavanones from Taiwanese Propolis, Journal, J.Nat. Prod., 2003, 66, 503-506, American Chemical Society and American Society of Pharmacognosy.
Anna Lisa Piccinelli et al, Phenolic Constituents and Antioxidant Activity of Wendita calysina Leaves (Burrito) a Fold Paraguayan Tea, Journal, J. Agric. Food Chem, 2004, 52, 5863-5868, American Chemical Society.
Ping Zhao et al., Efficient production and capture of 8-prenylnaringenin and leachianone G- biosynthetic intermediates of sophoraflavanone G—by the addition of cork tissue to cell suspension cultures of Sophora flavescens, Journal, Phytochemistry 62, 2003, 1093-1099, Elsevier Science Ltd.
Toshio Fukai et al., lsoprenylated Flavanones from Morus Cathayana, Journal, Phytochemistry, vol. 47, No. 2, pp. 273-280, 1998, Elsevier Science Ltd.
Chia-Nan Chen et al., Comparison of Radical Scavenging Activity, Cytotoxic Effects and Apoptosis Induction in Human Melanoma Cells by Taiwanese Propolis from Different Sources, Journal, Advance Access Publication, Aug. 18, 2004, eCAM, 2004:175-185, Oxford University Press.

*Primary Examiner*—Bernard Dentz
(74) *Attorney, Agent, or Firm*—WPAT, P.C.; Anthony King; Kay Yang

(57)    ABSTRACT

Disclosed is a compound capable of promoting the growth and development of neurons, the proliferation of neural stem cells and inducing the neural stem cells to differentiate into neurons, which is represented by a general formula as (I).

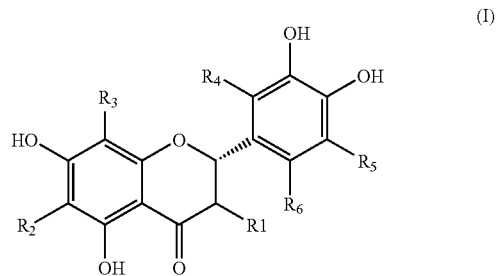

(I)

The compound of the present invention can increase the survival rate of neural cells even at a low cellular density in a culture medium. The compound of the present invention can also promote the growth of neurons, which is revealed by the increase in the thickness, length and number of branches in the neurites (neural fibers). In addition, the compound of the present invention can be used to promote the development of neural stem cells and induce them to differentiate into neurons.

4 Claims, 7 Drawing Sheets

COMPOUND FOR PROMOTING THE GROWTH OF NEURAL CELLS

BACKGROUND OF THE INVENTION

1. Field of the Invention

The present invention relates to a compound for promoting regeneration and differentiation of neural stem cells.

2. The Prior Arts

Neural stem cells (NSCs) are characterized as undifferentiated cells that have the capacity to self-renew and differentiate into other neural cells such as neurons, astrocytes and oligodendrocytes. NSCs can renew and differentiate in the presence of stimulating factors under in vitro cultural conditions. These differentiated cells play important roles during the development of central nervous system in mammals and also in the function of the fully developed nervous system in animals. NSCs can be isolated from the cortex of the brain of many mammals (such as mice, rats, pigs and humans) during their development before maturation. The NSCs in the central nervous system of humans are similar to those of rodents.

NSCs in mammals are present in mature organs as well as in the developing central nervous system. At the moment, one can also isolate neural stem cells from the embryonic brain of mammals; however, little is known on the mechanism of regulating endogenous neural stem cells.

The best method of treating a neurodegenerative disease is to restore and regenerate damaged or lost neural cells. Treatments in progress include replacing damaged cells through NSCs transplantation or activating endogenous NSCs in dormancy to "self-renew".

Although scientists have some knowledge of using NSCs to restore damaged neural cells, they need to find a way to effectively control them as they grow and differentiate into function-defined cells. Previous reports indicate that NSCs could propagate in a medium supplemented with growth factors such as basic Fibroblast Growth Factor (bFGF), Epithelial Growth Factor (EGF), etc. It is also known that in the presence of these growth factors in a serum-free medium, NSCs grown in suspension have the propensity to aggregate and form so-called "neurospheres". In addition, if these growth factors are removed and subsequently replaced with proper amount of known mitogenic factors, growth factors other than bFGF and EGF, or other neurotrophic factors, NSCs would most likely be stimulated into differentiation. The majority of the differentiated cells would be astrocytes (>90%), and only a few of them are neurons (<10%).

Many neurotrophic factors have been discovered in the past: Glial-derived Neurotrophic Factor (GDNF), Brain-derived Neurotrophic Factor (BDNF), Nerve Growth Factor (NGF), Neurotrophin-3 (NT3), Neurotrophin-4 (NT4), Platelet-derived Growth Factor (PDGF), and so on. Although these neurotrophic factors have been proven to promote the survival of neural cells, their clinical applications are limited. One reason is that their large molecular size prohibits them from passing the blood brain barrier (BBB).

If small molecular compounds could be found with the capability to activate endogenous NSCs, promote their growth and maintain their specificity, or even promote their differentiation into function able neurons, effective treatment or prevention of neurodegenerative diseases might become feasible. Through the effect of these compounds the success rate of NSCs transplantation into subjects may be improved.

SUMMARY OF THE INVENTION

To overcome the shortcomings of the prior art, the primary objective of the present invention is to provide a compound for promoting the growth of cortical neurons and NSCs, which has a small molecular size capable of passing blood brain barrier and reaching the brain more easily than large neurotrophic factors, to increase the survival rate of neural cells.

Another objective of the present invention is to provide a compound for promoting the differentiation of NSCs into neurons with specific functions.

To approach the above objectives, the present invention provides a prenylflavanone compound represented by a general formula as (I) shown below:

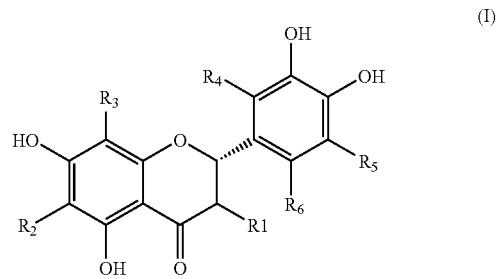

wherein, $R_1$ represents —H, —OH, a linear or branched alkyl group with 1 to 3 carbon atoms, or an isoprene group; $R_2$, $R_3$, $R_4$, $R_5$, $R_6$ and $R_7$ represent —H, —OH, a linear or branched alkyl group with 1 to 3 carbon atoms, an isoprene group or a geranyl group represented by formula (II) or formula (III), respectively.

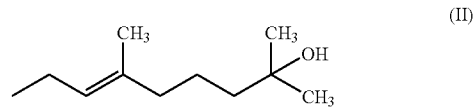

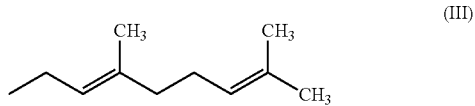

Cortical neurons cultured at low density (<160 cells/mm²) are known to die more frequently than those cultured at higher densities. The compound of the present invention not only increases the survival rate of cortical neurons, but also significantly decreases the death rate of cells in low-density cultures. The compound of the present invention can be used to promote the growth of cortical neurons, as evidenced by the thickness and length of their neurites. In addition, the compound of the present invention can also be used to promote the formation of NSCs and induce them to differentiate into neurons.

The present invention is further explained in the following embodiments. The present invention disclosed here is not limited by these examples. The present invention may be improved upon or modified by people skilled in the art and all such variations are not outside the scope and spirit of the present invention.

DETAILED DESCRIPTION OF THE PREFERRED EMBODIMENT

Figure 1:
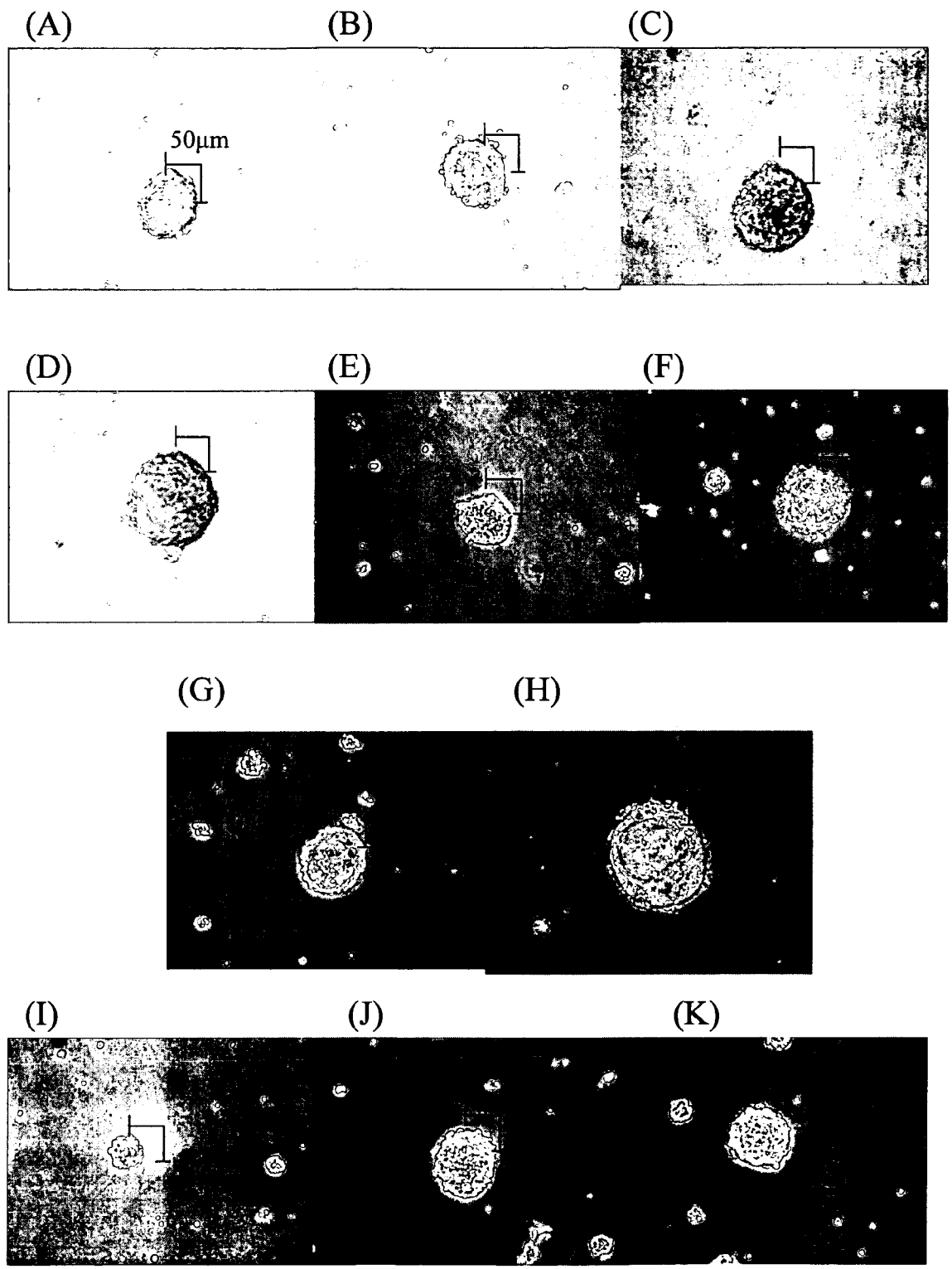
FIG. 1 shows photos on the appearance of NSCs after cultivation with media containing the compounds of the present invention or the known growth factors; (A) compound A; (B) compound B; (C) compound C; (D) compound D; (E) compound E; (F) compound F; (G) compound G; (H) compound H; (I) control group; (J) EGF, and (K) NGF.

The compound for promoting the proliferation of neural cell of the present invention is a prenylflavanone compound represented by a general formula as (I) shown below:

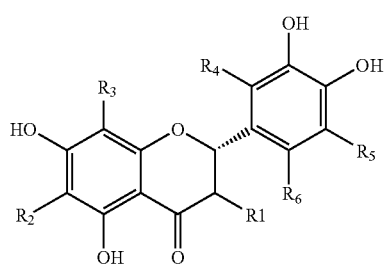

(I)

wherein R$_1$ represents —H, —OH, a linear or branched alkyl group with 1 to 3 carbon atoms, or an isoprene group; R$_2$, R$_3$, R$_4$, R$_5$, R$_6$ and R$_7$ represent —H, —OH, a linear or branched alkyl group with 1 to 3 carbon atoms, an isoprene group or a geranyl group represented by formula (II) or formula (III), respectively.

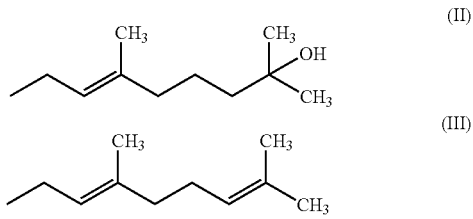

(II)

(III)

The prenylflavanone compound of the present invention can either be prepared from the known synthetic technology of Organic Chemistry, or from partial chemical modification on the functional groups of the similar compounds isolated from natural resources.

The examples of the prenylflavanone compound of the present invention are further represented by one of the following formulas (IV) to (XI):

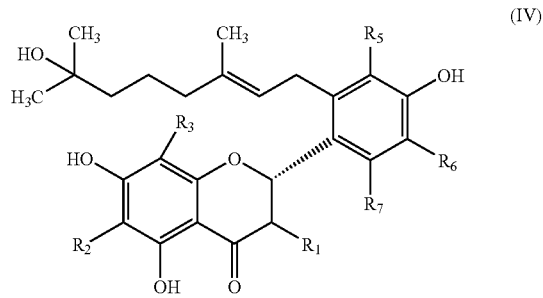

(IV)

wherein, R$_1$, R$_2$, R$_3$, R$_5$, R$_6$ and R$_7$ represent —H, —OH, a linear or branched alkyl group with 1 to 3 carbon atoms, or an isoprene group, respectively.

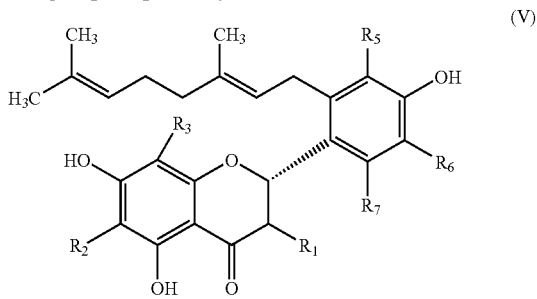

(V)

wherein, R$_1$, R$_2$, R$_3$, R$_5$, R$_6$ and R$_7$ represent —H, —OH, a linear or branched alkyl group with 1 to 3 carbon atoms, or an isoprene group, respectively.

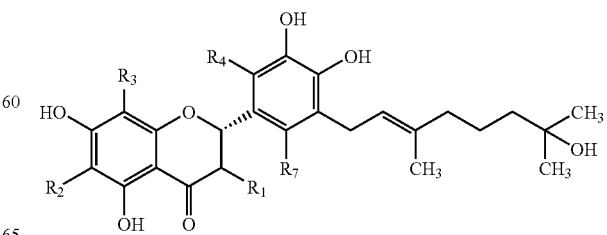

(VI)

wherein, $R_1$, $R_2$, $R_3$, $R_4$, $R_5$, and $R_7$ represent —H, —OH, a linear or branched alkyl group with 1 to 3 carbon atoms, or an isoprene group, respectively.

(VII)

wherein, $R_1$, $R_2$, $R_3$, $R_4$, $R_5$, and $R_7$ represent —H, —OH, a linear or branched alkyl group with 1 to 3 carbon atoms, or an isoprene group, respectively.

(VIII)

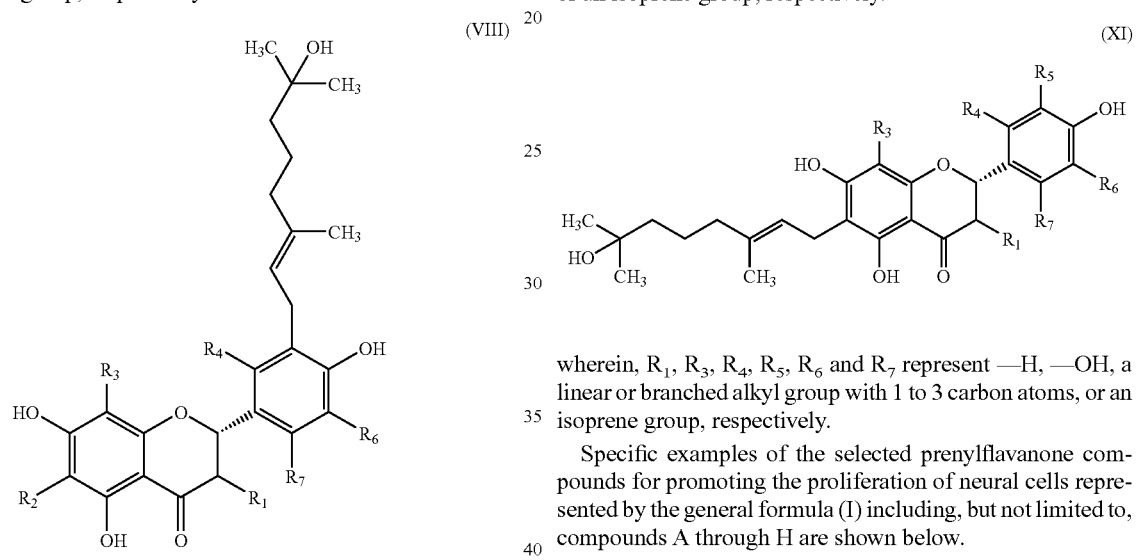

wherein, $R_1$, $R_2$, $R_3$, $R_4$, $R_6$ and $R_7$ represent —H, —OH, a linear or branched alkyl group with 1 to 3 carbon atoms, or an isoprene group, respectively.

(IX)

wherein, $R_1$, $R_2$, $R_3$, $R_4$, $R_6$ and $R_7$ represent —H, —OH, a linear or branched alkyl group with 1 to 3 carbon atoms, or an isoprene group, respectively.

(X)

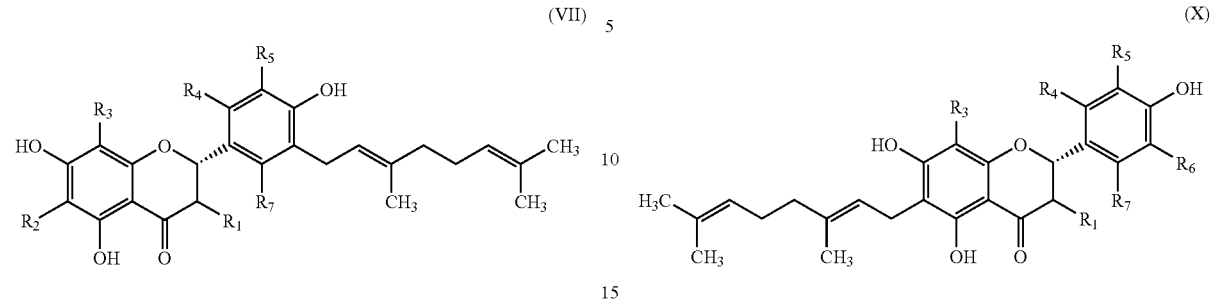

wherein, $R_1$, $R_3$, $R_4$, $R_5$, $R_6$ and $R_7$ represent —H, —OH, a linear or branched alkyl collection with 1 to 3 carbon atoms, or an isoprene group, respectively.

(XI)

wherein, $R_1$, $R_3$, $R_4$, $R_5$, $R_6$ and $R_7$ represent —H, —OH, a linear or branched alkyl group with 1 to 3 carbon atoms, or an isoprene group, respectively.

Specific examples of the selected prenylflavanone compounds for promoting the proliferation of neural cells represented by the general formula (I) including, but not limited to, compounds A through H are shown below.

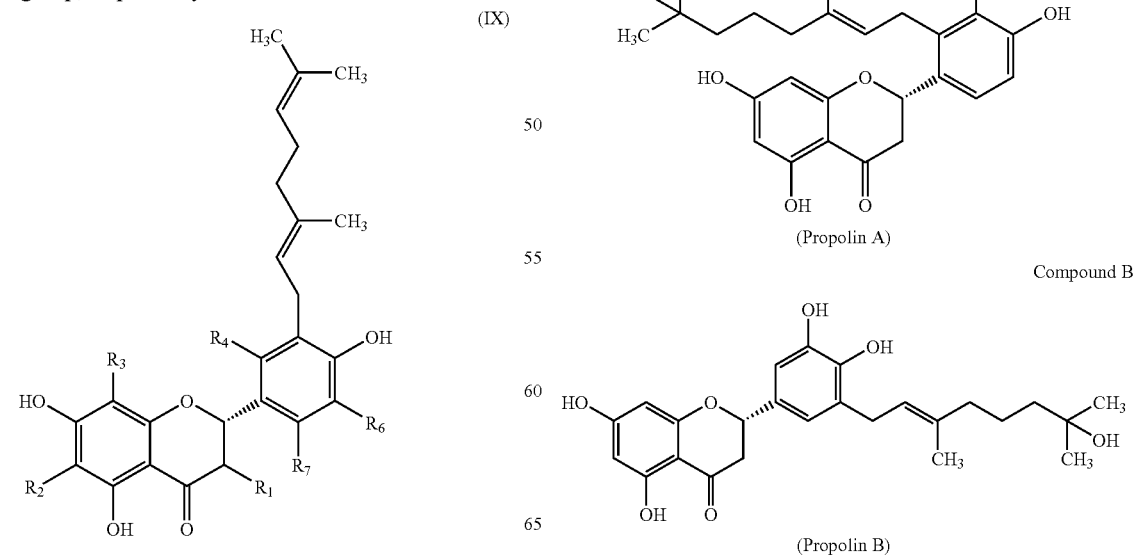

Compound A (Propolin A)

Compound B (Propolin B)

-continued

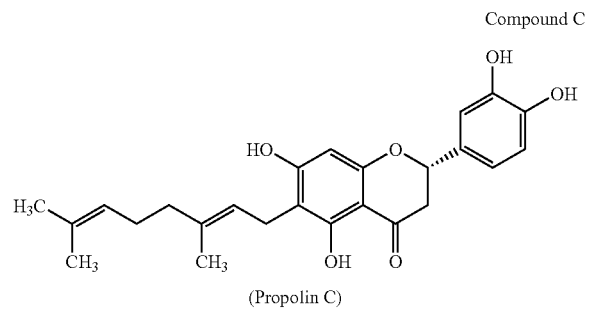
(Propolin C)

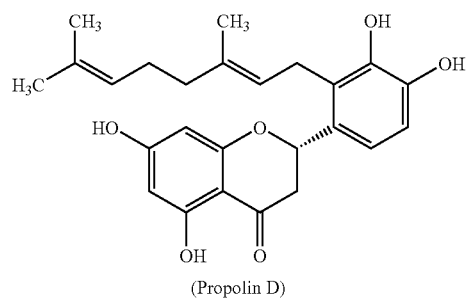
(Propolin D)

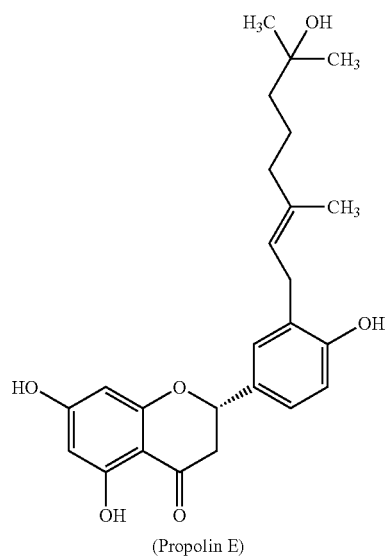
(Propolin E)

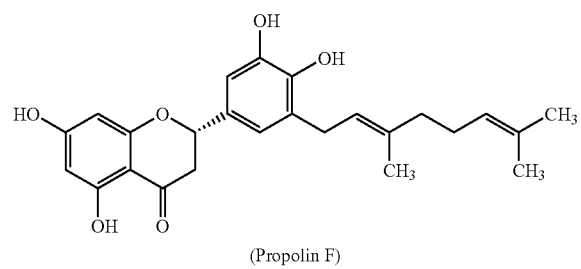
(Propolin F)

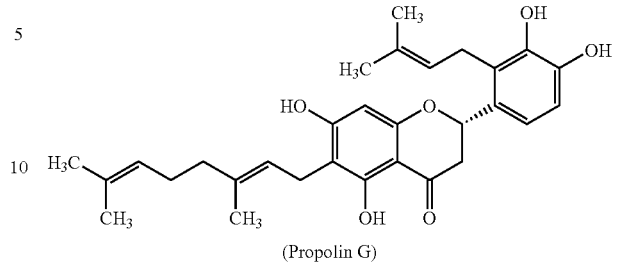
(Propolin G)

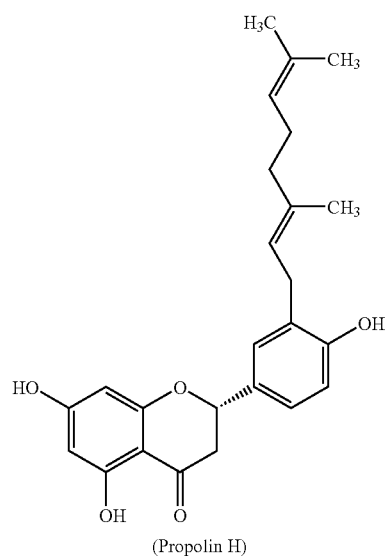
(Propolin H)

The compound of the present invention has the following features:

(1) The compound of the present invention can significantly maintain the growth of and reduce the death rate of neural cells (such as cortical neural cells) when they are cultivated at low cellular densities (<160 cells/mm$^2$). This makes the compound of the present invention novel and desirable supplements to the growth media used in neurological studies.

(2) The compound of the present invention can affect the growth of NSCs and produce thicker and longer neurites with more branches than bFGF or EGF can. This may play important roles in regenerating damaged or lost cells in neurodegenerative diseases such as Alzheimer's, Parkinson's, stroke, Lou Gehrig's, etc., and demyelinating or dysmyelinaing disorders such as multiple sclerosis. The compound of the present invention can be used individually or in combination with other compounds for such purposes.

(3) The compound of the present invention, while proliferating NSCs, can form neurospheres more effectively than bFGF or EGF and maintain the spheres in live condition for at least 30 days in vitro, making the compound of the present invention preferable to known growth factors for growth media. Furthermore, the neurospheres can be induced to differentiate into neurons, astrocytes and oligodendrocytes. Besides improving the viability of NSCs before and after transplantation, the compound of the present invention would also be useful for transforming these cells into function able cells.

(4) The compound of the present invention can induce the neural stem cells to form mainly neuronal stem cells and further differentiate mostly into neurons amounting to a level previously unobtainable: previous arts obtain only 20-30% whereas the compound of the invention can reach over 60% neurons (data not shown). Also, the compound of the present invention can be used in combination with one of the known growth factors such as bFGF to increase the proliferation of neural stem cells such that large numbers of neuronal stem cells can be produced for cell therapies in neurodegenerative diseases. Alternatively, by conventional techniques, this invention may produce, harvest, and purify large numbers of "naked" neural stem cells to be used in cell transplantation.

With different functions and characteristics from the large protein molecules used in prior arts (such as EGF, bFGF, GDNF, BDNF, NGF, NT3, NT4, PDGF and so on), the compound of the invention can be used as supplements for in vitro culture of NSCs and cortical neurons. The prenylflavanone compounds of the present invention are smaller molecules and are able to maintain their activity longer (replacement of the media can be done in about 7 to 9 days vs. 3-4 days). In addition, they can induce NSCs to differentiate into a large number of neurons. People who skilled in the art will easily understand through reading the above-mentioned description of the specification, the compound of the present invention can be used along with a growth factor in a culture medium to cultivate NSCs in order to promote the proliferation of the cells. The growth factors include, but are not limited to, EGF, bFGF, and nerve growth factor. The present invention provides a more beneficial supplement for the serum-free culture media used in the neurological studies in laboratories.

It is known that the small molecules can pass the Blood Brain Barrier (BBB) and reach the brain more easily than large molecules. Recently the Food and Drug Administration (FDA) of the United States approved stem cell transplantation therapy in humans, especially for the treatment of neurodegenerative diseases. Being small molecules able to induce the production of functional neurons in a serum-free medium and enhance the survival of neural cells at a low cellular density, the prenylflavanone compounds of the present invention can be used to complement the stem cell transplantation therapy in human.

According to the effects mentioned above, people who skilled in the art will easily understand through reading the above-mentioned description of the specification, the compound of the present invention may further be developed into pharmaceutical drugs through the conventional technology.

EXAMPLE 1

The growth medium for NSCs was prepared by adding penicillin G, streptomycin sulphate and 0.5 mM of L-glutamine into B-27 supplemented neurobasal medium (Gibco).

The unborn fetus was taken out from fetal sac in the abdominal cavity of a 16-day pregnant Wistar rat under anesthesia. The cerebral tissue was removed from the fetus and treated with 0.1% trypsin solution for one minute at 25° C. After washing with PBS solution 3 times, cells were dissociated by the known mechanical method of up and down mixing. The resulting solution was passed through a 70 μm Nylon cell strainer (Falcon) in order to obtain the cerebral cells in the filtrate. The filtrate was centrifuged at 1000 rpm for 10 minutes and the supernatant was aspirated and the pellet re-suspended in the growth medium prepared above. The resulting suspension of the obtained cells contained NSCs.

The cells in the suspension were seeded at around 150,000 cells/ml onto 10-cm Petri dishes (10 ml was used). The cells were incubated at 37° C., 5% $CO_2$ and 95% relative humidity. The growth medium was replaced one half at a time, once every three days.

When cultivating the NSCs, the growth media were supplemented with either 5 ng/ml of EGF, 5 ng/ml of bFGF, or 5 ng/ml of NGF. These were used as the positive control group. In the experimental group, the growth media were supplemented with one of the compounds of the invention, A-H, respectively. The growth media with the addition of 5 μl of Dimethyl Sulfoxide (DMSO) were used as the vehicle control. The cells were incubated at the same condition as described above for 7 days and then observed under a microscope. The size and morphologic appearance of aggregated NSCs known as neurospheres were noted. FIG. 1 shows the results.

The results show that NSCs grown with the compounds A-H, EGF or NGF all form aggregates of cells known as neurospheres and the neurospheres formed are larger than those with the vehicle control. Therefore, the compounds of the present invention have the same effects as the known growth factors on promoting the growth of NSCs. That is, the compounds of the present invention have the effect of promoting the proliferation of NSCs.

EXAMPLE 2

Cells obtained from the suspension prepared in Example 1 were cultivated in 6-well plates coated with 30 μg/ml of poly-D-lysine (Sigma) at 300 cells/mm$^2$ and cultivated at 37° C., 5% $CO_2$ and 95% relative humidity. The growth media contained compounds A, B, D, E, F, G, and H respectively and the growth media added with 5 μl of DMSO were used as control. The differentiated cells after cultivation were categorically called cortical neurons.

The experiments were repeated three times. After cultivating for 5 days, live cells were counted by a known cell-counting method (MTT assay) and the absorbance was read at 540 nm. The results are shown in FIG. 2.

Figure 2:
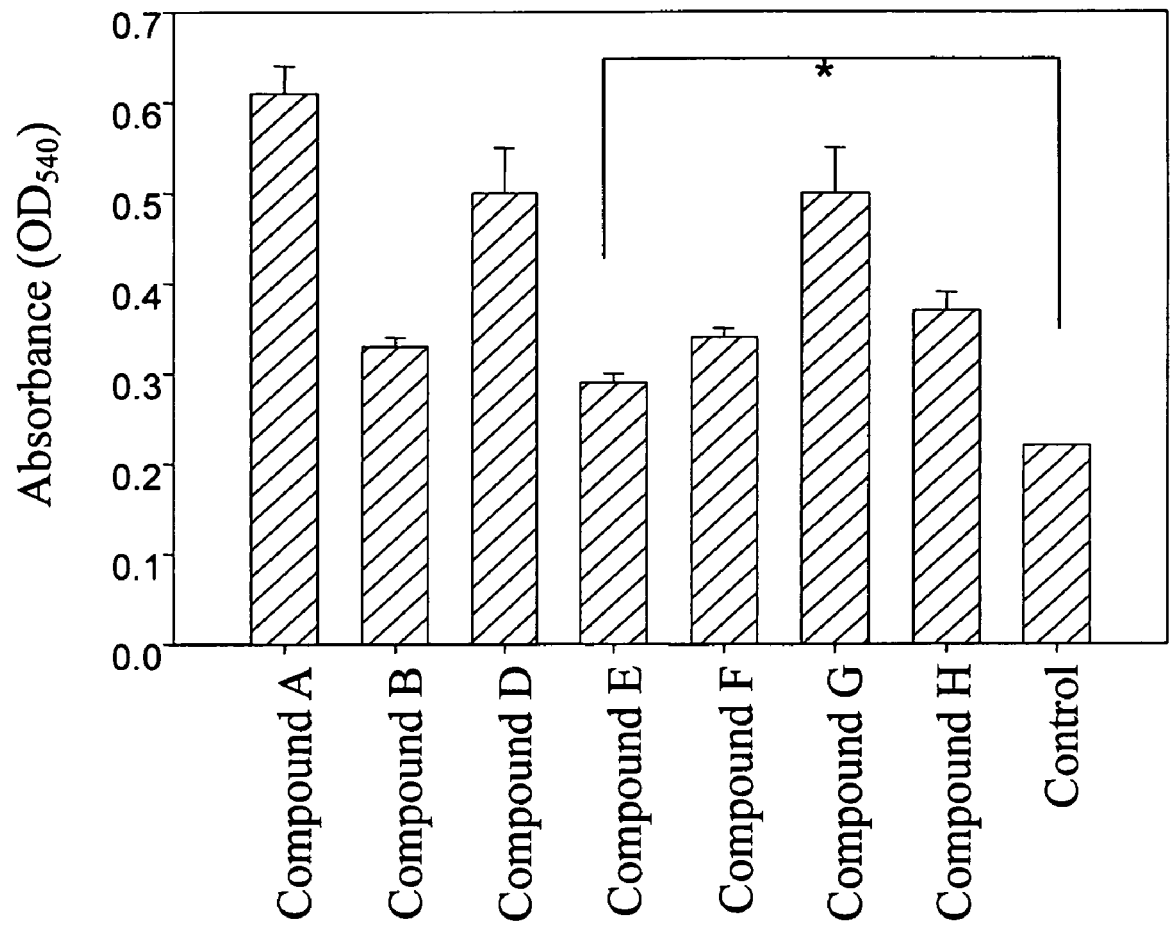
FIG. 2 shows the effects on the growth of cortical neurons after supplementing the media with the compounds of the present invention (* represents p<0.0005).

The results from FIG. 2 show that the absorbances of the experimental group are significantly higher than those of the control group; the best results are found with compound A, D, and G. The results show that the compounds of the invention increase the survival rate of cortical neurons significantly.

EXAMPLE 3

Cells obtained from the suspension prepared in Example 1 were cultivated at a density of 150 or 300 cells/mm$^2$ in 6-well plates coated with 30 μg/ml poly-D-lysine (Sigma) at 37° C., 5% $CO_2$ and 95% relative humidity. The growth media contained compounds A, D, and G respectively and the growth media added with 5 μl of DMSO were used as control. The differentiated cells are categorically called cortical neurons.

The experiments were repeated three times. After cultivating for 5 days, the live cells were counted by a known cell-counting method (MTT assay) and the absorbance was read at 540 nm. The results are shown in FIG. 3.

It has been known that the survival rate of cortical neurons cultivated at a cell density of 640 cells/mm$^2$ can be as high as greater than 90%; while cultivated at a cell density of 160 cells/mm$^2$ the survival rate drops down to around 50%. Therefore without adding any growth factor at proper time when cells are cultivated at less than 160 cells/mm$^2$ the death rate of the cells will greatly increase. This is due to the distance between cells at low densities being too far for them to transfer growth factors.

Figure 3:
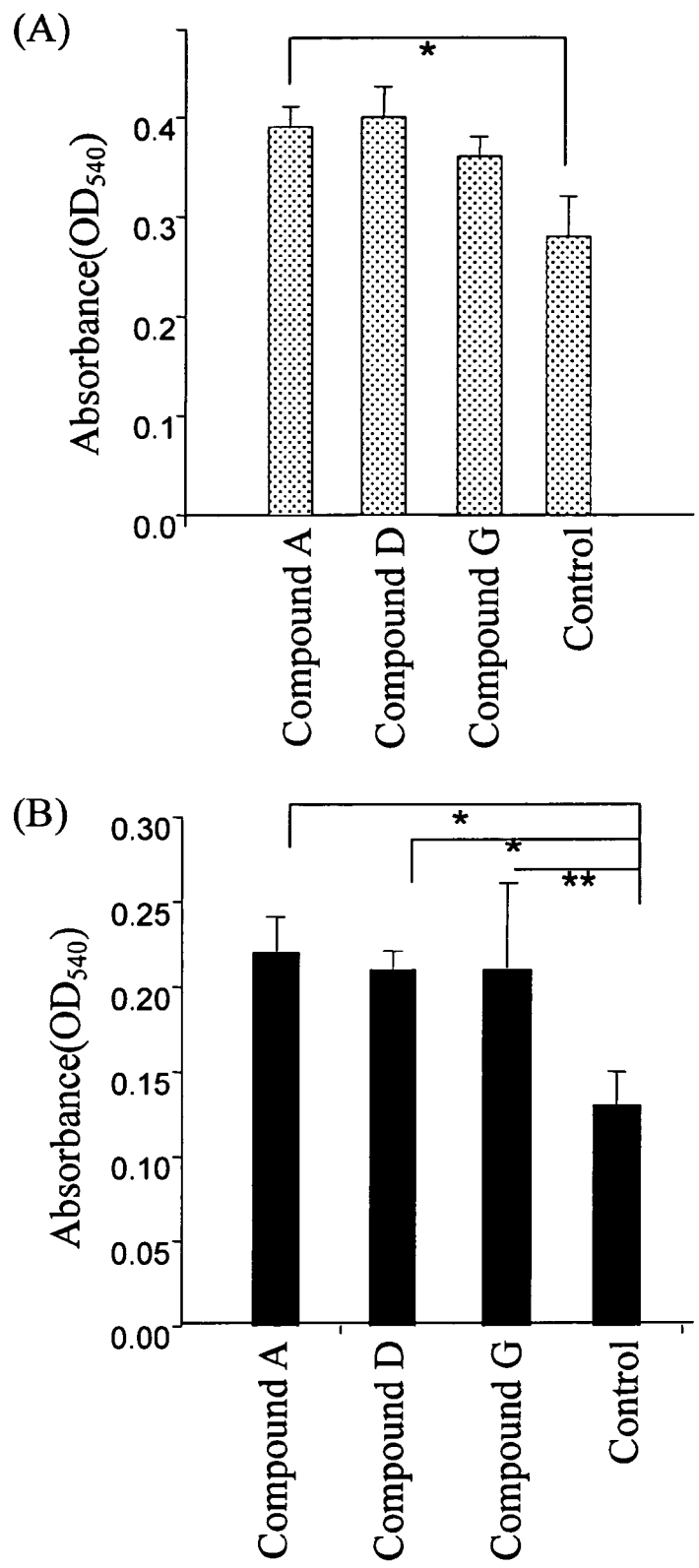
FIG. 3 shows the effects on the growth of cortical neural cells at different cell densities after supplementing the media with the compounds of the present invention (* represents p<0.005, ** represents p<0.05); (A) cell density at 300 cells/mm$^2$; (B) cell density at 150 cells/mm$^2$.

The results in FIG. 3 show that the absorbances of the experiment group are significantly higher than those of the control group no matter what the starting cell density is, indicating that the compounds of the present invention can significantly improve the survival rate of the cortical neurons when cultivated at low cellular densities.

EXAMPLE 4

Cells obtained from the suspension prepared in Example 1 were cultivated at a density of 38 cells/mm$^2$ in 6-well plates coated with 30 μg/ml poly-D-lysine (Sigma) at 37° C., 5% $CO_2$ and 95% relative humidity. The growth media contained compounds A, B, D, and G respectively and the growth media added with 5 μl of DMSO were used as control. The differentiated cells are categorically called cortical neurons.

The experiments were repeated three times. After cultivating for 5 days, the cells were observed under microscope and the length of the neurites was measured. The results are shown in FIG. 4.

Figure 4:
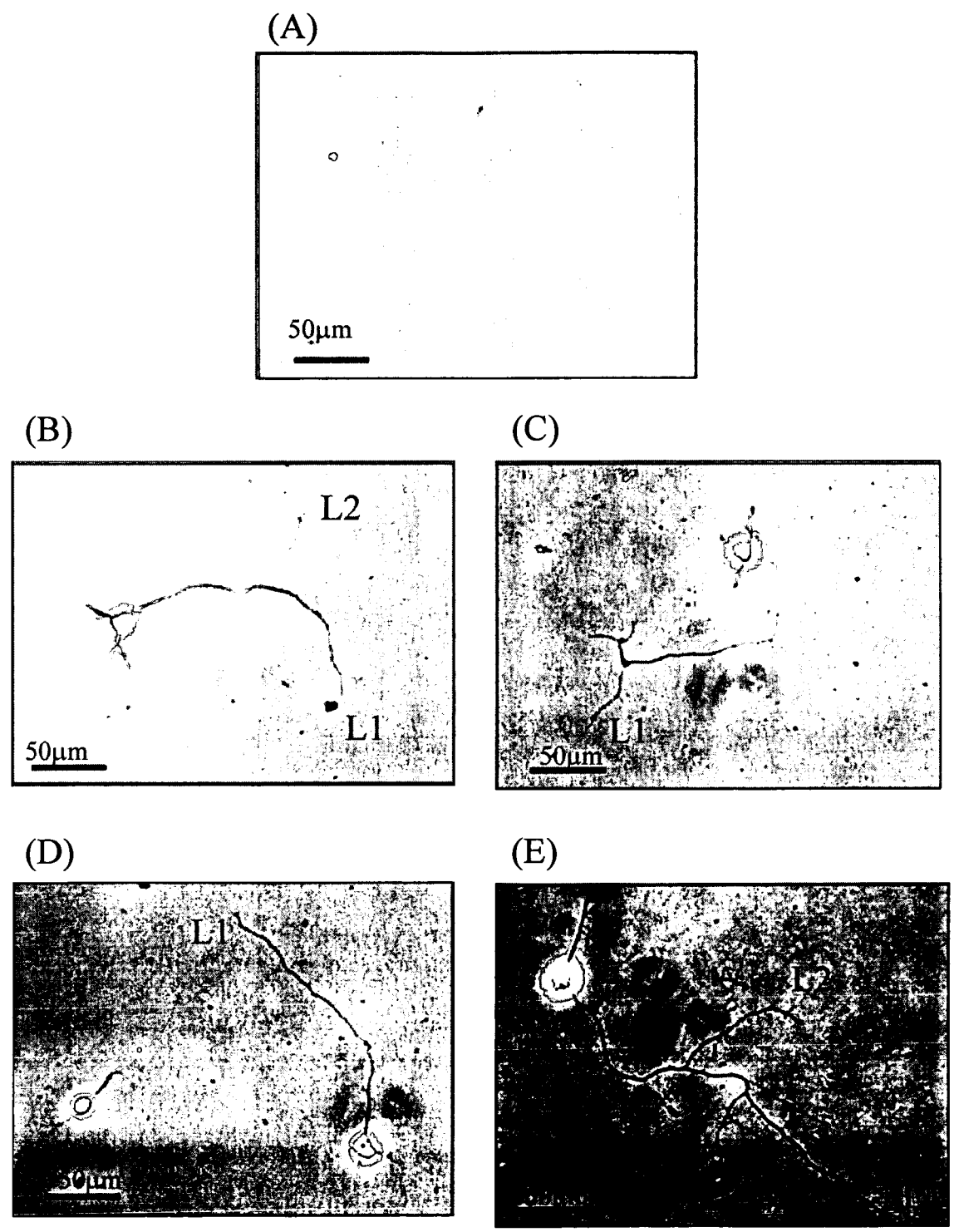
FIG. 4 shows the photos of the effects of the compounds of the present invention on the length of the neurites of the neuronal cells; (A) control group; (B) compound A; (C) compound B; (D) compound D, and (E) compound G.

FIG. 4 shows under the microscope the control group which was cultivated without any growth factor-all the neural cells are dead, atrophy of the soma of the neurons can be seen and the length of the neurites cannot be measured (FIG. 4A). Whereas cultivating with the addition of 2.5 μM of compound A, 5 μM of compound B, 5 μM of compound D, or 5 μM of compound G in the growth media respectively, under microscope the continuous growth of the neurons and the extension of the neurites can be observed. There are at least 3 neurites extending out of each soma and one of them lengthens and branches out with several dendrites at the terminal. The measurement of the lengths of neurites are: L1, 236 μm, L2, 161 μm, with compound A (FIG. 4B); L1, 235 μm, with compound B (FIG. 4C); L1, 211 μm, with compound D (FIG. 4D); and L, 316 μm, L2, 216 μm, with compound G (FIG. 4E).

These results indicate that the compounds of the present invention can improve the survival rates of neural cells when cultivated at a low cellular density (38 cells/mm$^2$), enhance the lengthening of neurites and induce neural cells to develop into mature neurons.

EXAMPLE 5

In the beginning of cultivating NSCs, either compound A or EGF was added into the growth media. The cells were cultivated for 3 days and the cells would aggregate to form neurospheres. One hundred μl of the cell suspension was aspirated and diluted to 1 ml. 250 μl of the supernatant which contained neurospheres was aspirated and placed on the cover slides coated with 30 μg/ml poly-D-lysine (Sigma). After all the cells had been attached onto the slides, the media was removed and replaced with the cultivating media containing compound A (FIG. 5A), EGF (FIG. 5C), or none of the growth factors (FIG. 5B, compound A in the beginning; FIG. 5D, EGF in the beginning). The cells were cultivated for another 3 days at the same condition as described above so that the cells would differentiate into cortical neurons.

The cells were stained with a known immunofluorescent staining method. To stain the neurons, a neurological marker of MAP-2 (microtubule-associated protein 2) antibody was used as the primary antibody and a fluorescent material-labeled mouse immunoglobulin that identified primary antibody was used as the second antibody. After the primary antibody that had been bound onto the neurons was identified and bound by the secondary antibody, the neurons emit fluorescent light under the excitation of a specific light source.

Figure 5:
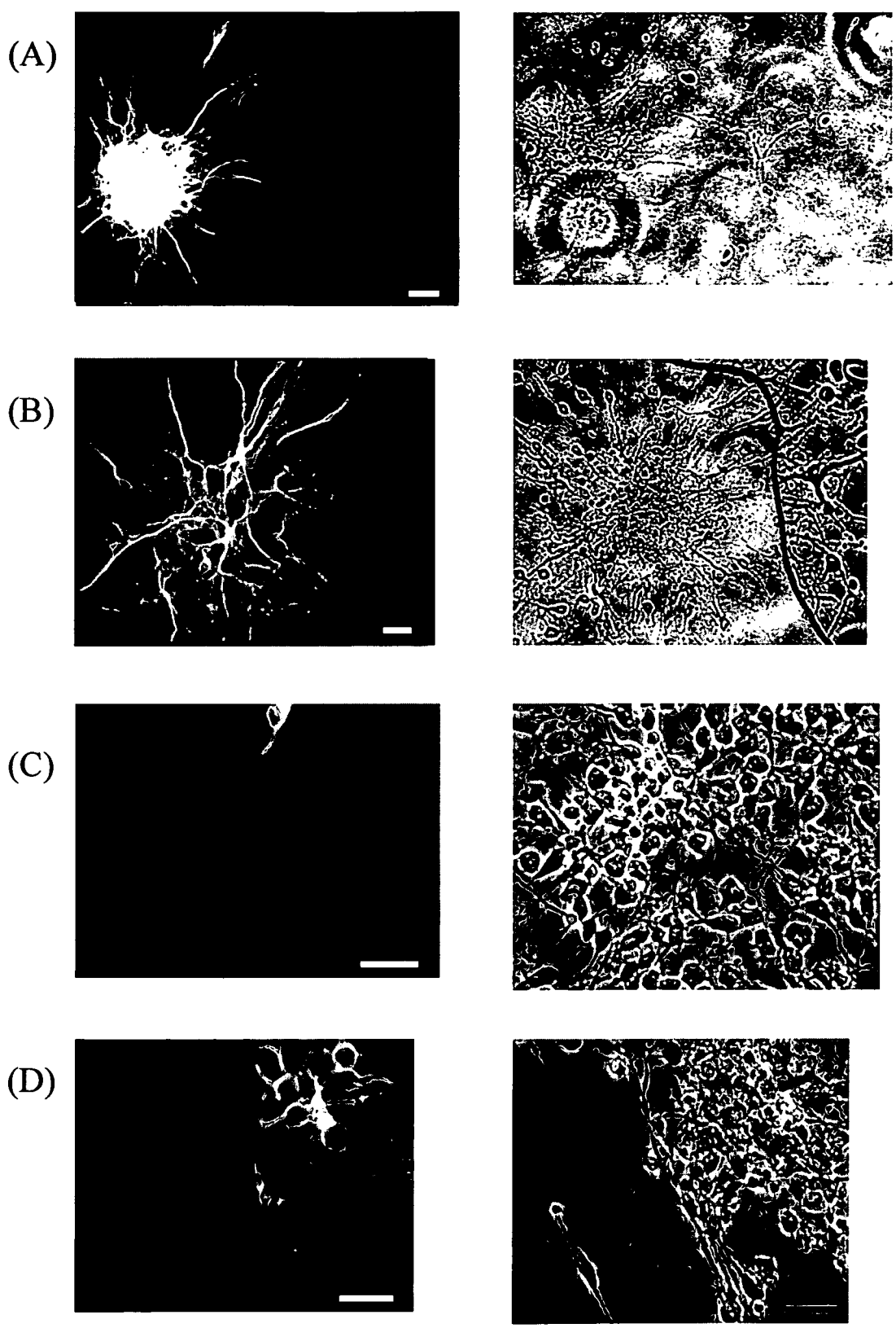
FIG. 5 shows microscopic photos of the resulted cell morphologies after inducing NSCs to differentiate. Photos with fluorescent emission are shown on the left and photos with visible light are shown on the right. (A) Cells were cultivated with compound A supplemented in the beginning and thereafter; (B) Cells were cultivated with compound A supplemented in the beginning and none thereafter; (C) Cells were cultivated with EGF supplemented in the beginning and thereafter; (D) Cells were cultivated with EGF supplemented in the beginning and none thereafter.

Referring to FIG. 5, in the left are photos under fluorescent excitation. Neurons are in white while dead or non-neuronal cells are in shade (in photo, fluorescent light reflected in white, non-fluorescent shown in the dark. Please see the attached photo in the left). In the right are photos under visible light, the morphology of all the cells in the field can be seen. Results shown in FIG. 5 indicate that when cultivating neural stem cells, if compound A is added to the culture media in the beginning, the cells will differentiate into neurons whether or not compound A is added again when the cells are seeded on the cover slides (FIG. 5A and FIG. 5B). Whether EGF is added both in the beginning and at seeding (FIG. 5C) or only in the beginning (FIG. 5D), the neural cells will proliferate and differentiate mostly into non-neuronal cells. The number of the cells proliferated is lower when EGF is only added in the beginning. (Please refer to the legends for the sequence of adding the factors) These results indicate that although EGF can be used to promote the proliferation of neural stem cells and increase their survival, the majority of the proliferated cells are non-neuronal progenitor cells. On the other hand, the compounds of the present invention not only can increase the survival of neural stem cells, but also affect their differentiation into neurons.

EXAMPLE 6

The procedures were similar to Example 5. However, in the beginning of cultivating the neural stem cells, both compound D and EGF were added into the media. After all the cells had been attached onto the slides, the media were removed and replaced with the cultivating media containing compound D (FIG. 6B), EGF (FIG. 6C), none of the growth factors (FIG. 6D), or both compound D and EGF (FIG. 6A). The cells were cultivated for another 3 days and the cell morphology was observed thereafter by using immunofluorescent staining technique.

Figure 6:
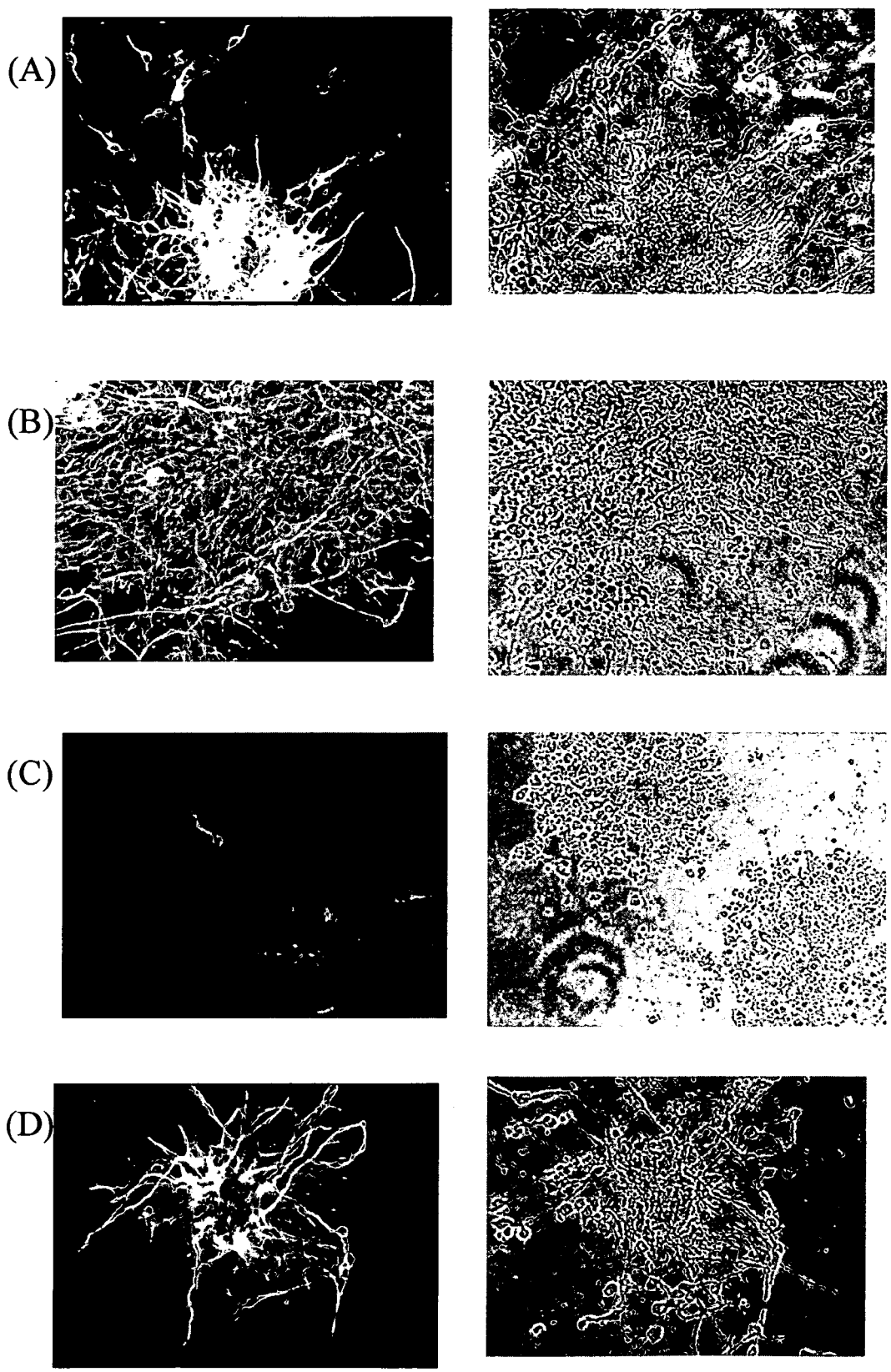
FIG. 6 shows microscopic photos of the resulted cell morphologies after inducing NSCs to differentiate. Photos with fluorescent emission are shown on the left and photos with visible light are shown on the right: (A) with both compound D and EGF supplemented in the beginning and thereafter; (B) with both compound D and EGF supplemented in the beginning and compound D thereafter; (C) with both compound D and EGF supplemented in the beginning and EGF thereafter; (D) with both compound D and EGF supplemented in the beginning and none supplemented thereafter.

Referring to FIG. 6, in the left are photos under fluorescent excitation. Neurons are in white while dead or non-neuronal cells are in shade. In the right are photos under visible light. The morphology of all the cells in the field can be seen. Results shown in FIG. 6 indicate that when cultivating neural stem cells, if compound D and EGF are both added in the beginning and when the cells are seeded, there is significant proliferation of neural stem cells and they specifically differentiate mostly into neurons (FIG. 6A). When EGF is added alone while the cells are seeded, the cells differentiated into non-neuronal cells (FIG. 6C) whereas when compound D is added, the cells will differentiate into neurons (FIG. 6B). When none of the growth factor is added, the cells will still differentiate into neurons but the number of cells is lower (FIG. 6D). In conclusion, EGF can promote the proliferation of neural cells, but only when combined with compound D can neural stem cells differentiate more discriminately into neurons after seeding. Furthermore, the results indicate that under the influence of compound D, neural stem cells can proliferate into neuronal stem cells that can further differentiate into neurons after seeding.

EXAMPLE 7

As in Example 1, the NSCs were cultivated continuously and the growth media were replaced every seven days. DMSO-added growth media were used as the negative control. After 30 days, 100 μl of the cell suspension was aspirated and diluted to 1 ml. 250 μl of the supernatant was aspirated and placed on the slides coated with 30 μg/ml poly-D-lysine (Sigma). The cell morphology was observed thereafter under a microscope. The results are shown in FIG. 7.

Figure 7:
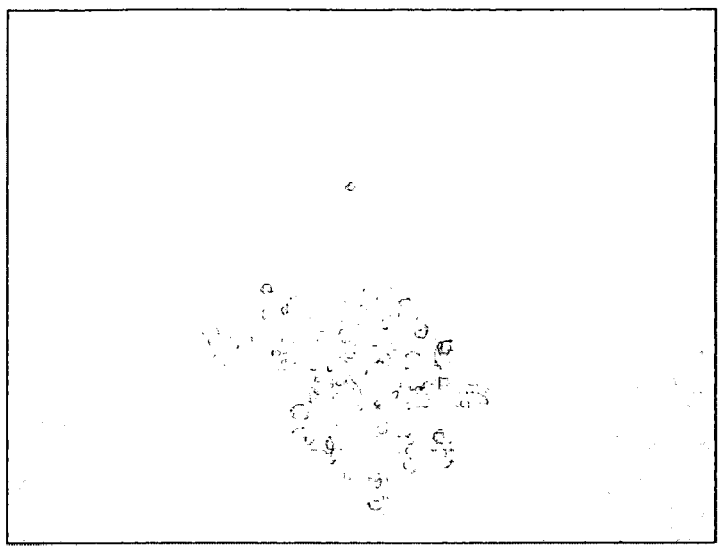
FIG. 7 shows microscopic photos of cell morphology after cultivating NSCs for 30 days; Neurospheres were analyzed by a phase contrast microscope: (A) control group, (B) supplemented with compound A, and (C) neurospheres produced with compound A supplementation were induced to differentiate by migration assay, immuno-stained with MAP-2, and analyzed by a fluorescence microscopy.
Figure 7:
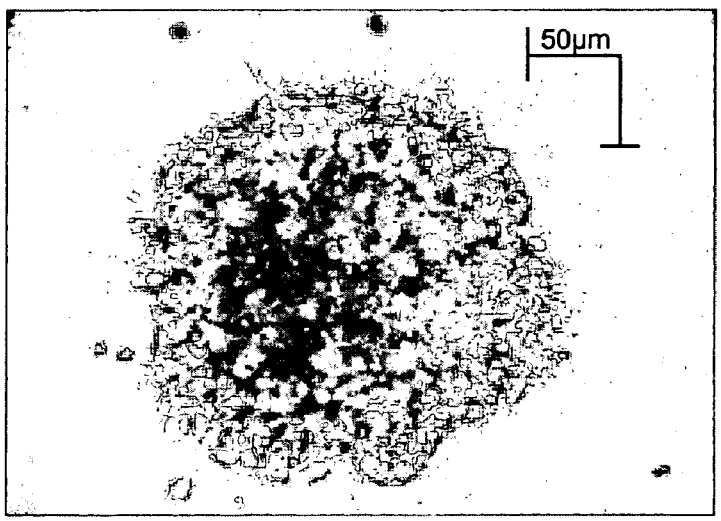
Figure 7:

The results in FIG. 7 show that almost no surviving cells are found in the control group in which none of the growth factors is added (FIG. 7A). Unlike the normal neural stem cells, the cells lose their propensity to aggregate and form spheres, and the cells become atrophic in the cultivating suspension. Neural stem cells grown with compound A, on the other hand, can maintain the characteristics of forming spherical clusters (FIG. 7B). These cells were cultivated for another 3 days and the cells were stained with immunofluorescence the same as in Example 5. Under microscope, the neural stem cells can still be seen differentiating normally into neurons with the continuous outgrowth of neurites (FIG. 7C).

From the embodiments shown above, the compounds of the present invention can be used to cultivate neural stem cells, maintain the characteristic of aggregating to form spheres, and induce the neural stem cells to differentiate into neurons. In addition, the compounds of the present invention can, during continuous cultivation, cultivate the cells for a longer time by replacing the growth media only once every 7 days and keep the neural stem cells alive for more than 30 days. The media with the known growth factors, however, have to be replaced once every 3-4 days because these growth factors are proteins that are all large molecules and tend to lose their bioactivity at room temperature. The compounds of the invention are small molecules and have no such attribute.

What is claimed is:

1. A method for stimulating the proliferation of neuron stem cells (NSCs), inducing the NSCs to differentiate into neurons, and promoting the growth and development of neurons, comprising administrating a subject in need thereof an effective amount of a pharmaceutical composition comprising a compound selected from the group consisting of the following:

(a) a compound represented by a general formula (IV):

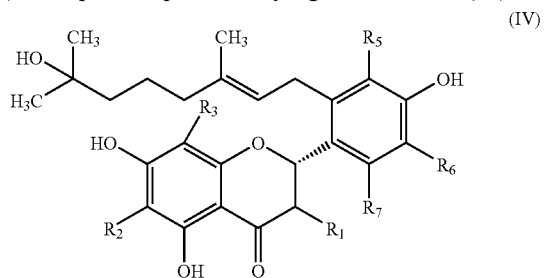

(IV)

wherein, $R_1$, $R_2$, $R_3$, $R_5$, $R_6$ and $R_7$ represent —H, —OH, a linear or branched alkyl group with 1 to 3 carbon atoms, or an isoprene group, respectively;

(b) a compound represented by a general formula (V):

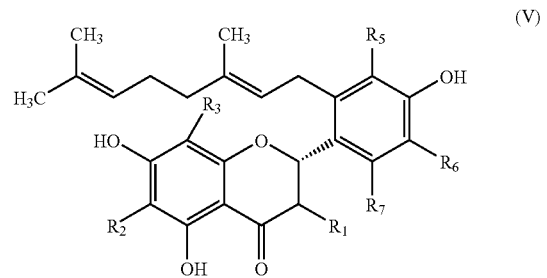

(V)

wherein, $R_1$, $R_2$, $R_3$, $R_5$, $R_6$ and $R_7$ represent —H, —OH, a linear or branched alkyl group with 1 to 3 carbon atoms, or an isoprene group, respectively;

(c) a compound represented by a general formula (VI):

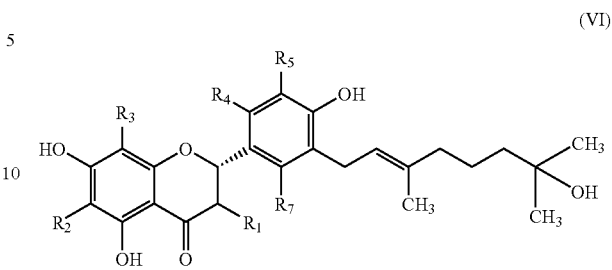

(VI)

wherein, $R_1$, $R_2$, $R_3$, $R_4$, $R_5$, and $R_7$ represent —H, —OH, a linear or branched alkyl group with 1 to 3 carbon atoms, or an isoprene group, respectively;

(d) a compound represented by a general formula (VII):

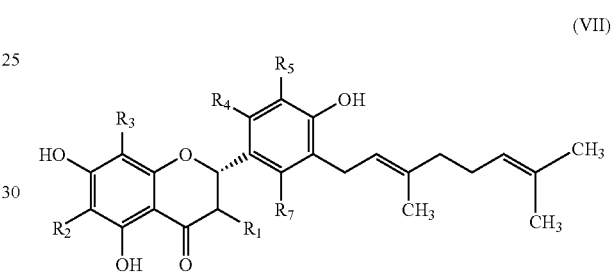

(VII)

wherein, $R_1$, $R_2$, $R_3$, $R_4$, $R_5$, and $R_7$ represent —H, —OH, a linear or branched alkyl group with 1 to 3 carbon atoms, or an isoprene group, respectively;

(e) a compound represented by a general formula (VIII):

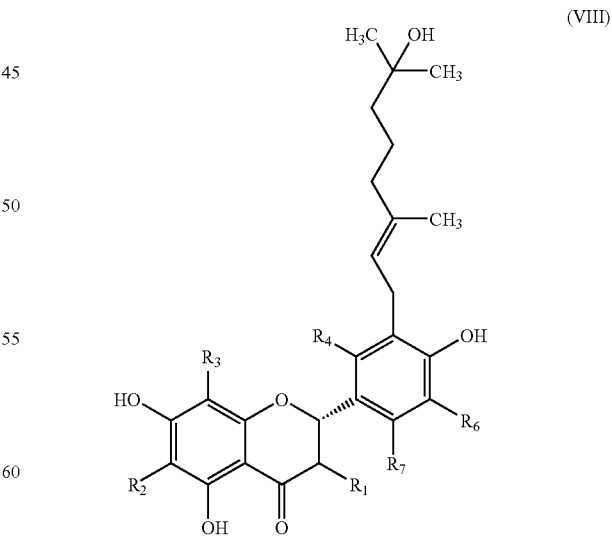

(VIII)

wherein, $R_1$, $R_2$, $R_3$, $R_4$, $R_6$ and $R_7$ represent —H, —OH, a linear or branched alkyl group with 1 to 3 carbon atoms, or an isoprene group, respectively;

(f) a compound represented by a general formula (IX):

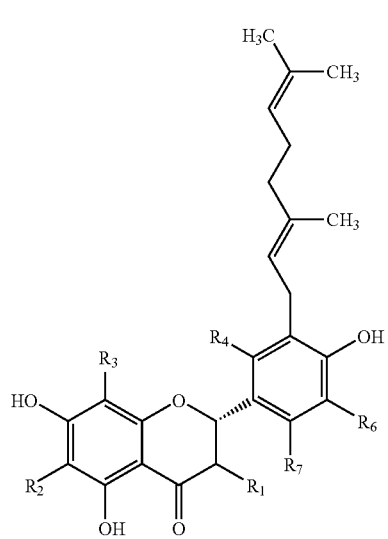

wherein, $R_1$, $R_2$, $R_3$, $R_4$, $R_6$ and $R_7$ represent —H, —OH, a linear or branched alkyl group with 1 to 3 carbon atoms, or an isoprene group, respectively;

(g) a compound represented by a general formula (X):

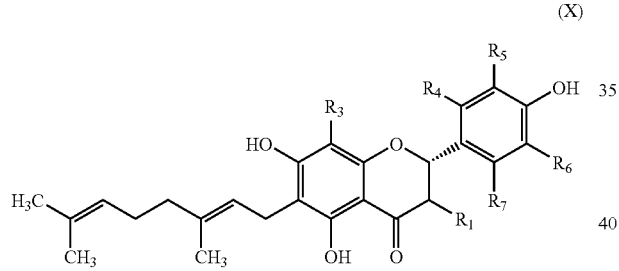

wherein, $R_1$, $R_3$, $R_4$, $R_5$, $R_6$ and $R_7$ represent —H, —OH, a linear or branched alkyl group with 1 to 3 carbon atoms, or an isoprene group, respectively; and (h) a compound represented by a general formula (XI):

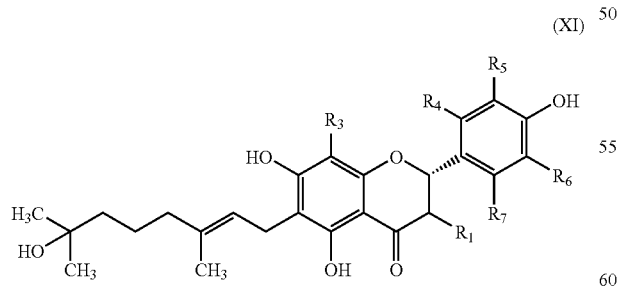

wherein, $R_1$, $R_3$, $R_4$, $R_5$, $R_6$ and $R_7$ represent —H, —OH, a linear or branched alkyl group with 1 to 3 carbon atoms, or an isoprene group, respectively.

2. The method according to claim 1, wherein the compound is selected from the group consisting of:

Compound A (Propolin A)

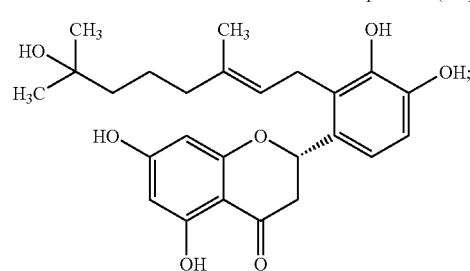

Compound B (Propolin B)

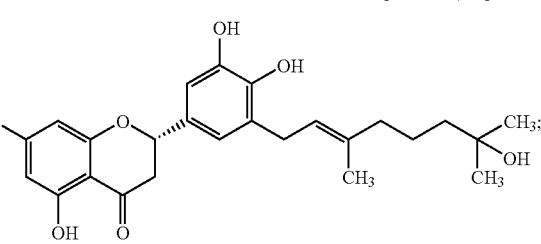

Compound C (Propolin C)

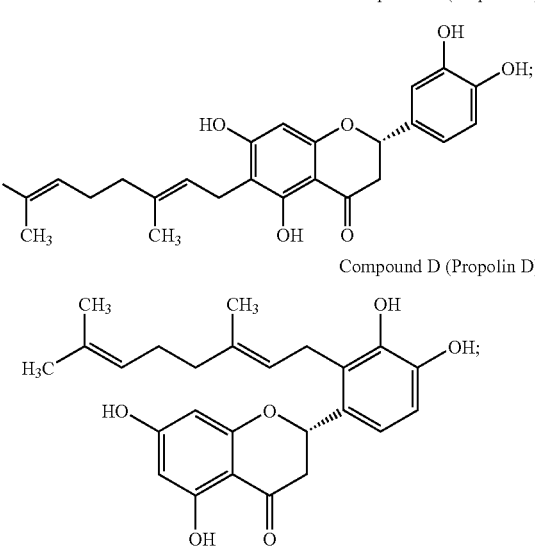

Compound D (Propolin D)

Compound E (Propolin E)

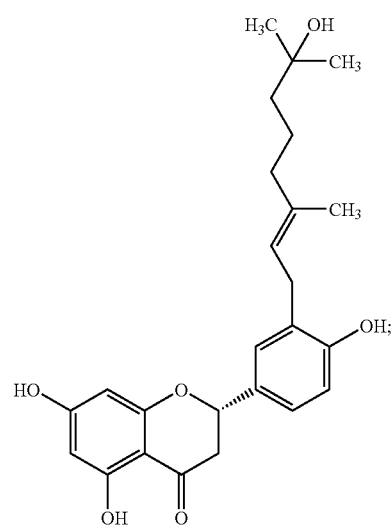

-continued

Compound F (Propolin F)

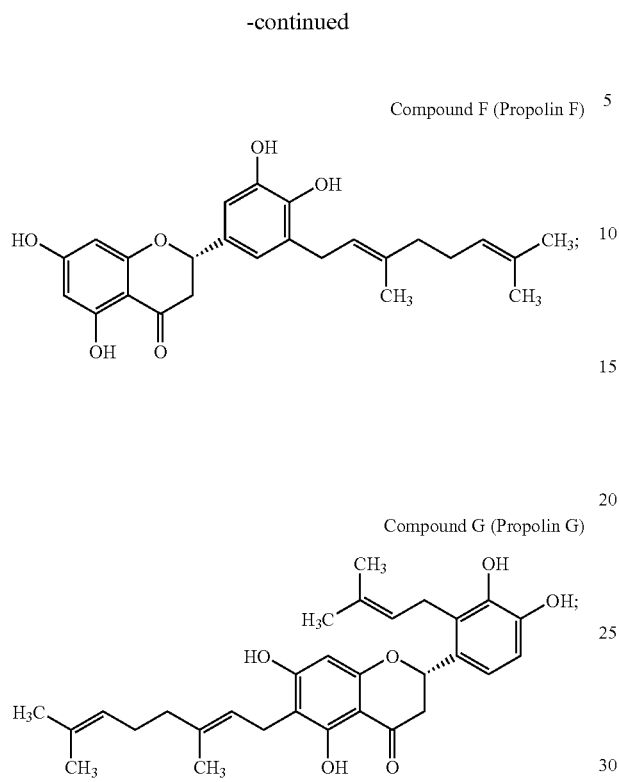

Compound G (Propolin G)

-continued
and

Compound H (Propolin H)

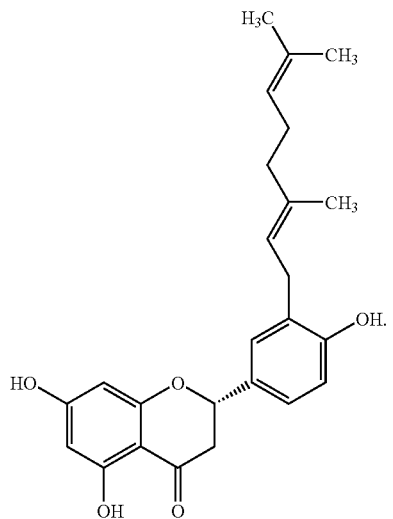

3. The method according to claim 1, wherein the pharmaceutical composition further comprises a growth factor.

4. The method according to claim 3, wherein the growth factor is selected from the group consisting of Epithelial Growth Factor (EGF), basic Fibroblast Growth Factor (bFGF) and nerve growth factor (NGF).

* * * * *